United States Patent
Tang et al.

(10) Patent No.: US 9,278,903 B2
(45) Date of Patent: Mar. 8, 2016

(54) CRYSTAL FORM OF PROSTAGLANDIN ANALOGUE, AND PREPARATION METHOD AND USE THEREOF

(71) Applicant: Shanghai Techwell Biopharmaceutical Co., Ltd., Shanghai (CN)

(72) Inventors: Zhijun Tang, Shanghai (CN); Yubin Liu, Shanghai (CN); Bingming He, Shanghai (CN); Jun Yang, Shanghai (CN); Xiaoming Ji, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 14/371,405

(22) PCT Filed: Jan. 10, 2013

(86) PCT No.: PCT/CN2013/070296
§ 371 (c)(1),
(2) Date: Jul. 9, 2014

(87) PCT Pub. No.: WO2013/104318
PCT Pub. Date: Jul. 18, 2013

(65) Prior Publication Data
US 2015/0005384 A1    Jan. 1, 2015

(30) Foreign Application Priority Data

Jan. 10, 2012 (CN) .......................... 2012 1 0006216

(51) Int. Cl.
C07C 59/72 (2006.01)
C07C 51/43 (2006.01)
(52) U.S. Cl.
CPC .................. C07C 59/72 (2013.01); C07C 51/43 (2013.01); C07C 2103/14 (2013.01)
(58) Field of Classification Search
None
See application file for complete search history.

(56) References Cited

U.S. PATENT DOCUMENTS

| 4,486,598 | A | 12/1984 | Aristoff |
| 2007/0254032 | A1 | 11/2007 | Kidane et al. |
| 2012/0283470 | A1* | 11/2012 | Batra et al. .................... 562/466 |

FOREIGN PATENT DOCUMENTS

| WO | 2005/007081 A2 | 1/2005 |
| WO | 2009/078965 A1 | 6/2009 |
| WO | 2009/137066 A1 | 11/2009 |
| WO | 2010/129757 A1 | 11/2010 |
| WO | 2012/088607 A1 | 7/2012 |

OTHER PUBLICATIONS

Hong, Bor-Cherng et al., "Intramolecular Diels-Alder Cycloadditions of Fulvenes. Application to the Kigelionol, Neomphilectane, and Kempane Skeletons," *Org. Lett.* (2005) 7(4):557-560.
Moriarty, Robert M. et al., "The Intramolecular Asymmetric Pauson-Khand Cyclization as a Novel and General Steroselective Route to Benzindene Prostacyclins: Synthesis of UT-15 (Treprostinil)," *J. Org. Chem.* (2004) 69(6):1890-1902.
International Search Report (English Translation) corresponding to PCT/CN2013/070296 mailed Apr. 18, 2013 (6 pages).

* cited by examiner

Primary Examiner — Clinton Brooks
Assistant Examiner — Jennifer C Sawyer
(74) Attorney, Agent, or Firm — Kilpatrick Townsend & Stockton LLP

(57) ABSTRACT

Provided are a crystal form A of a compound having the structure as represented by formula I, and preparation method and use thereof. The X-ray powder diffraction (XRPD) chart of the crystal form A has characteristic peaks at the following diffraction angles: 2.9±0.2°, 13.6±0.2°, 17.3±0.2° and 18.6±0.2°.

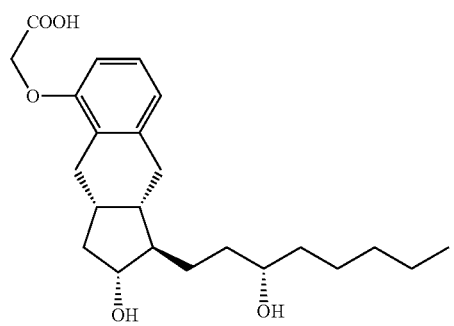

13 Claims, 4 Drawing Sheets

CRYSTAL FORM OF PROSTAGLANDIN ANALOGUE, AND PREPARATION METHOD AND USE THEREOF

TECHNICAL FIELD

This invention relates to chemical pharmaceutical fields, especially to a crystalline form of prostaglandin analogues and the preparation as well as the use thereof.

BACKGROUND

Treprostinil (UT15) is a class of novel drugs for treating pulmonary hypertension with the structure of formula I:

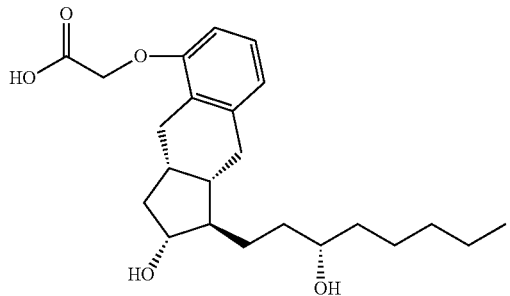

Pulmonary arterial hypertension (PAH) is a disease mainly characterized in pulmonary arteriola vasospasm, intimal hyperplasia and remodeling. Vascular proliferation of pulmonary arteriola and remodeling will lead to progressive increase in pulmonary vascular resistance, and ultimately right ventricular failure and death.

Epoprostenol (Flolan) is the first prostacyclin drug approved by U.S. Food and Drug Administration (FDA) for treating PAH. Half-life of Epoprostenol in circulation is about 3-5 mins, continuous intravenous administration is necessary, and it should be cryopreserved before infusion.

Treprostinil is an epoprostenol analog. The compound is stable under physiological conditions, and was the first developed drug for continuous subcutaneous injection. Compared with intravenous administration of epoprostenol, subcutaneous injection of treprostinil appears safer and more convenient. Inhaled formulations thereof has also been approved by FDA. Treprostinil was described in U.S. Pat. No. 4,306,075 for the first time. Treprostinil and other prostacyclin derivatives have been prepared according to Moriarty et al., J. Org. Chem. 2004, 69, 1890-1902, Drug of the Future, 2001, 26 (4), 364-374, U.S. Pat. Nos. 6,441,245, 6,528,688, 6,765,117, 6,809,223 and 6,756,117.

It is described in U.S. Pat. No. 5,153,222 that treprostinil is applicable to treat pulmonary hypertension. Treprostinil was approved for intravenous and subcutaneous injection, and the latter avoids continuous intravenous catheter-related sepsis events. U.S. Pat. Nos. 6,521,212 and 6,756,033 describe the treatment of pulmonary hypertension, peripheral vascular disease, as well as other diseases and symptoms by inhalation of treprostinil. U.S. Pat. No. 6,803,386 discloses the treatment of cancer by administrating treprostinil. U.S. Patent Application Publication No. 2005/0165111 discloses the treatment of ischemic lesions by using treprostinil. U.S. Pat. No. 7,199,157 discloses the improvement of renal function by using treprostinil. U.S. Patent Application Publication No. 2005/0282903 discloses the treatment of neuropathic foot ulcers by using treprostinil. U.S. application Ser. No. 12/028,471 discloses the treatment of pulmonary fibrosis by using treprostinil. U.S. Pat. No. 6,054,486 discloses the use of treprostinil for treating peripheral vascular disease. U.S. patent application Ser. No. 11/873,645 discloses a combination therapy including treprostinil. U.S. Application Publication No. 2008/0200449 discloses the delivery of treprostinil by using a dose-metered inhaler. U.S. Application Publication No. 2008/0280986 discloses the treatment of interstitial lung disease by using treprostinil. U.S. application Ser. No. 12/028,471 discloses the treatment of asthma by using treprostinil. U.S. Pat. Nos. 7,417,070, 7,384,978 and U.S. Application Publication No. 2007/0078095, 2005/0282901 and 2008/0249167 describe the oral dosage form of treprostinil and other prostacyclin analogues.

In the prior art, there are few reports regarding the crystals and purification of Treprostinil, wherein the literature (J. Org Chem 2004, 69, 1890-1902) reported a ethanol-water system for recrystallization of UT15; WO2009137066 reported a monohydrate treprostinil; and both of crystallization methods are similar and employ ethanol-water system. The inventors have prepared the crude compound I according to the method reported in the literature (J. Org. Chem. 2004, 69, 1890-1902) and obtained a slightly yellow gummy solid, however, the reaction liquids are difficult to be filtered and the residual solvent can not be completely removed under reduced pressure. Then, the obtained product was recrystallized using ethanol-water system, and dried under reduced pressure to give an extremely viscous substance. Such substance remains viscous after being stored at low-temperature (−20° C. to 0° C.), and no solidification or crystallization occurs at all.

Generally, prostaglandins have poor stability, and should be stored below −20° C. In view of the stability and purity of the compound, there is an urgent need in the art to obtain a stable crystal form of compound I.

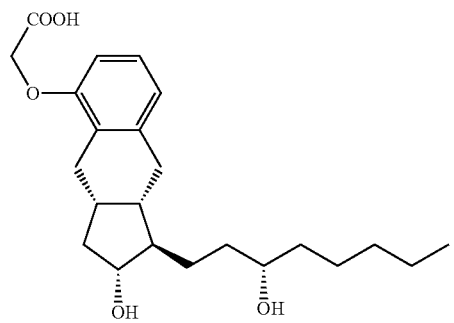

SUMMARY OF THE INVENTION

The purpose of the present invention is to provide a novel and stable crystalline form of compound I.

Another purpose of the present invention is to provide a preparation method for the novel crystalline form of compound I.

Another purpose of the present invention is to provide the use of the novel crystalline form of compound I.

The fourth purpose of the present invention is to provide a pharmaceutical composition comprising the novel crystalline form of compound I.

In the first aspect of the present invention, crystalline form A of a compound is provided, wherein the compound has the structure of formula I, and said crystalline form A has characteristic peaks at the following 2θ angles in the X-ray Powder diffraction (XRPD) pattern: 2.9±0.2°, 13.6±0.2°, 17.3±0.2° and 18.6±0.2°;

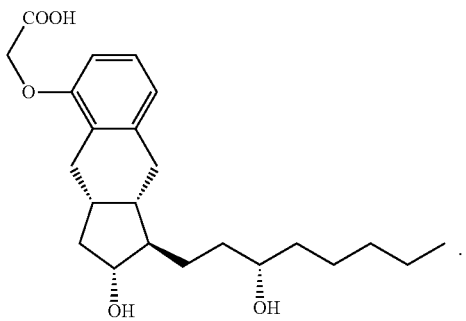

I

Preferably, said crystalline form A may has other characteristic peak at the following 2θ angle in the X-ray powder diffraction pattern: 21.8±0.2°.

The maximum peak in the differential scanning calorimetry (DSC) for the crystalline form A of the compound provided by the invention exists at 123° C.-128° C.; preferably, at 125° C.; and more preferably, the differential scanning calorimetry (DSC) for the crystalline form A is shown as in FIG. 2.

Infrared Spectrum of said crystalline form A of the compound provided by the invention is shown in FIG. 3.

In the second aspect of the present invention, a preparation method for the crystalline form A of compound I is provided, comprising the following steps:

(1) the crude compound of formula I is mixed with one or more solvents selected from following solvent 1 to obtain solution 1: methanol, acetonitrile, ethyl acetate, methyl acetate, isopropyl acetate, and t-butyl acetate;

(2) solution 1 is stirred and cooled, or solvent 2 is added to give the crystalline form A of compound I provided by the invention, wherein said solvent 2 is selected from one or more of the following: water, C5-C8 alkane.

In step (1) of the above preparation method, the temperature for mixing is at 0-80° C.; preferably, at 20-50° C.; more preferably, at 30-50° C.

In step (1) of the above preparation method, the weight to volume ratio for mixing the crude compound of formula I and solvent 1 is 1:0.5-50 (g:ml); preferably, 1:0.5-20 (g:ml); and more preferably, 1:1-5 (g:ml).

In step (2) of the above preparation method, the temperature is cooled to −25° C. to 25° C.; preferably, to −5° C. to 5° C.; and more preferably, to −2° C. to 2° C.

In step (2) of the above preparation method, after cooled, solution 1 is stirred for 5-50 hours; preferably, 10-30 hours; and more preferably, 12-25 hours.

In the above preparation method, the volume ratio of solvent 2 in steps (2) to solvent 1 in step (1) is 0.1-1:1; preferably, 0.2-0.8:1; and more preferably, 0.4-0.6:1.

In step (2) of the above preparation method, after solvent 2 is added, the resulting mixture is cooled to 1 to 10° C., and then is stirred for 5-50 hours; and preferably, cooled to 3 to 7° C., and then is stirred for 10-30 hours.

In the third aspect of the present invention, a pharmaceutical composition is provided, said pharmaceutical composition comprising crystalline form A of compound I provided by the invention and a pharmaceutically acceptable carrier.

In the fourth aspect of the present invention, the use of crystalline form A of compound I as said above is provided, for preparing pharmaceutical composition for treating pulmonary arterial hypertension and peripheral vascular disease.

Based on the above, a stable crystalline form of compound I is obtained by the present invention.

| Peak | 2-θ | d (A) | I % (Relative Intensity) |
|------|--------|---------|--------------------------|
| 1 | 2.960 | 29.8272 | 100 |
| 2 | 6.520 | 13.5453 | 10.3 |
| 3 | 13.520 | 6.5437 | 22.8 |
| 4 | 17.319 | 5.1159 | 24.5 |
| 5 | 18.581 | 4.7713 | 26.6 |
| 6 | 21.722 | 4.0880 | 18.3 |

Figure 2:
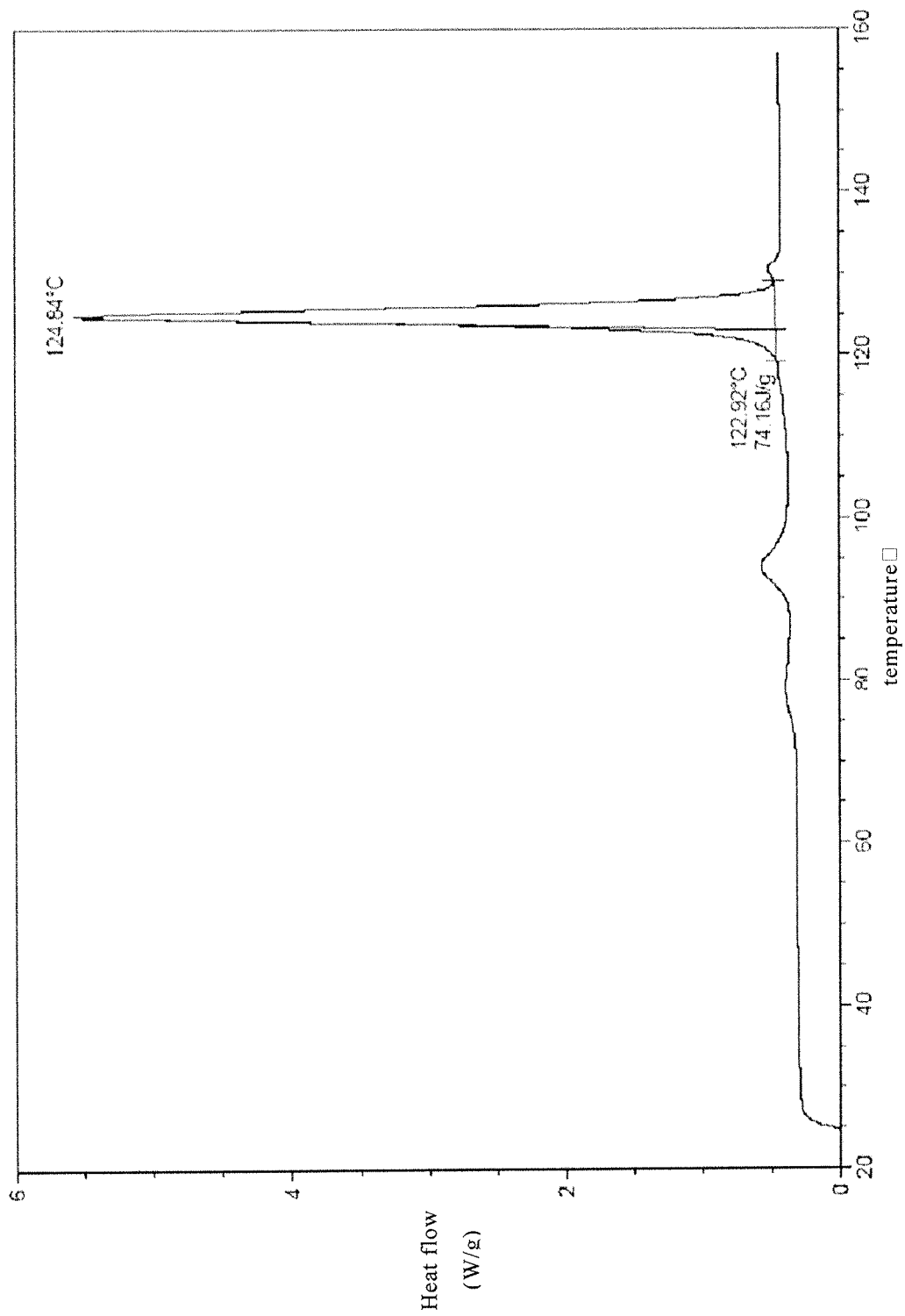

FIG. 2 is the differential scanning calorimetry (DSC) of crystalline form A of compound I obtained in Examples of the invention.

Figure 3:
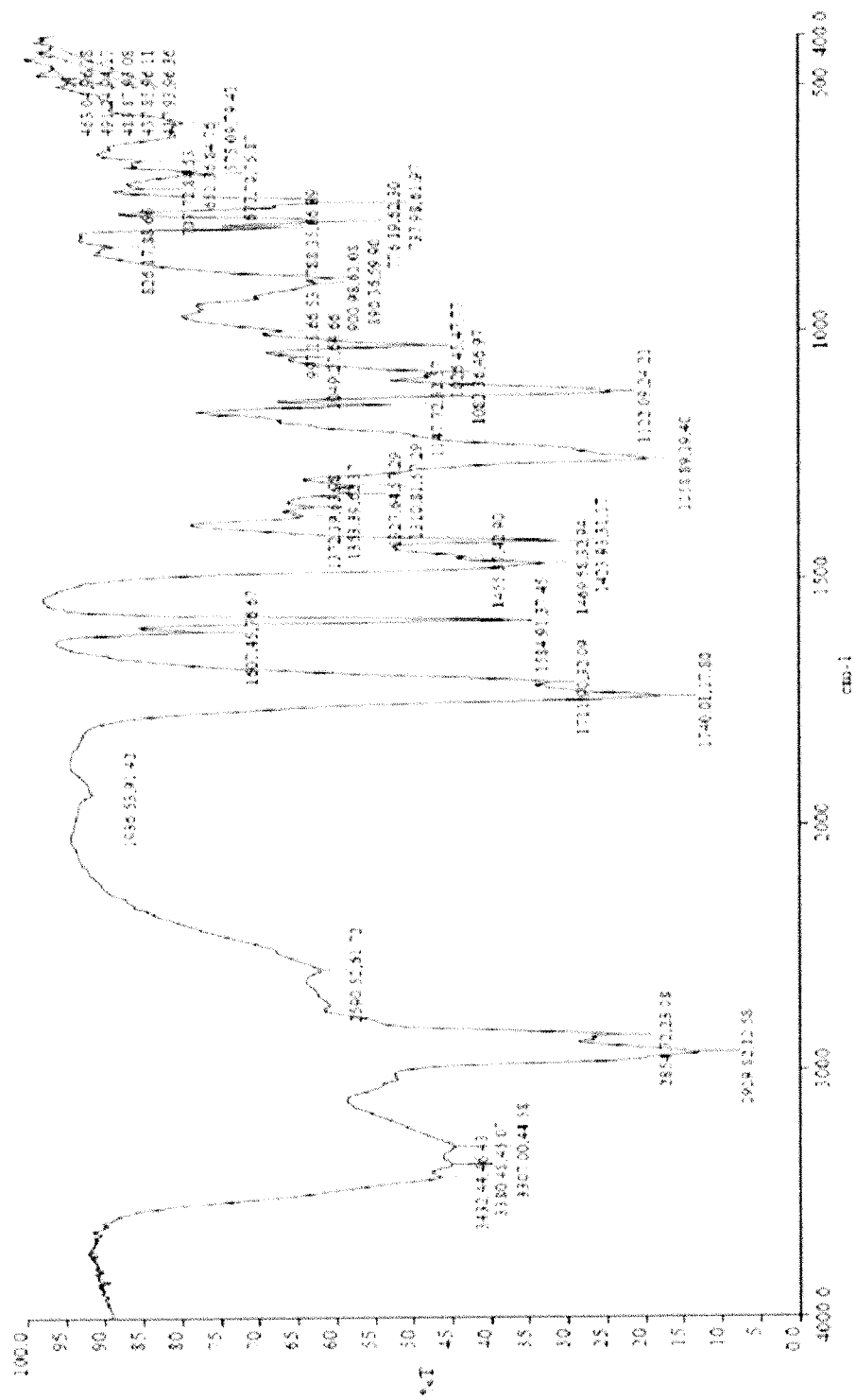

FIG. 3 is the Infrared Spectrum (IR) of crystalline form A of compound I obtained in Examples of the invention.

Figure 4:
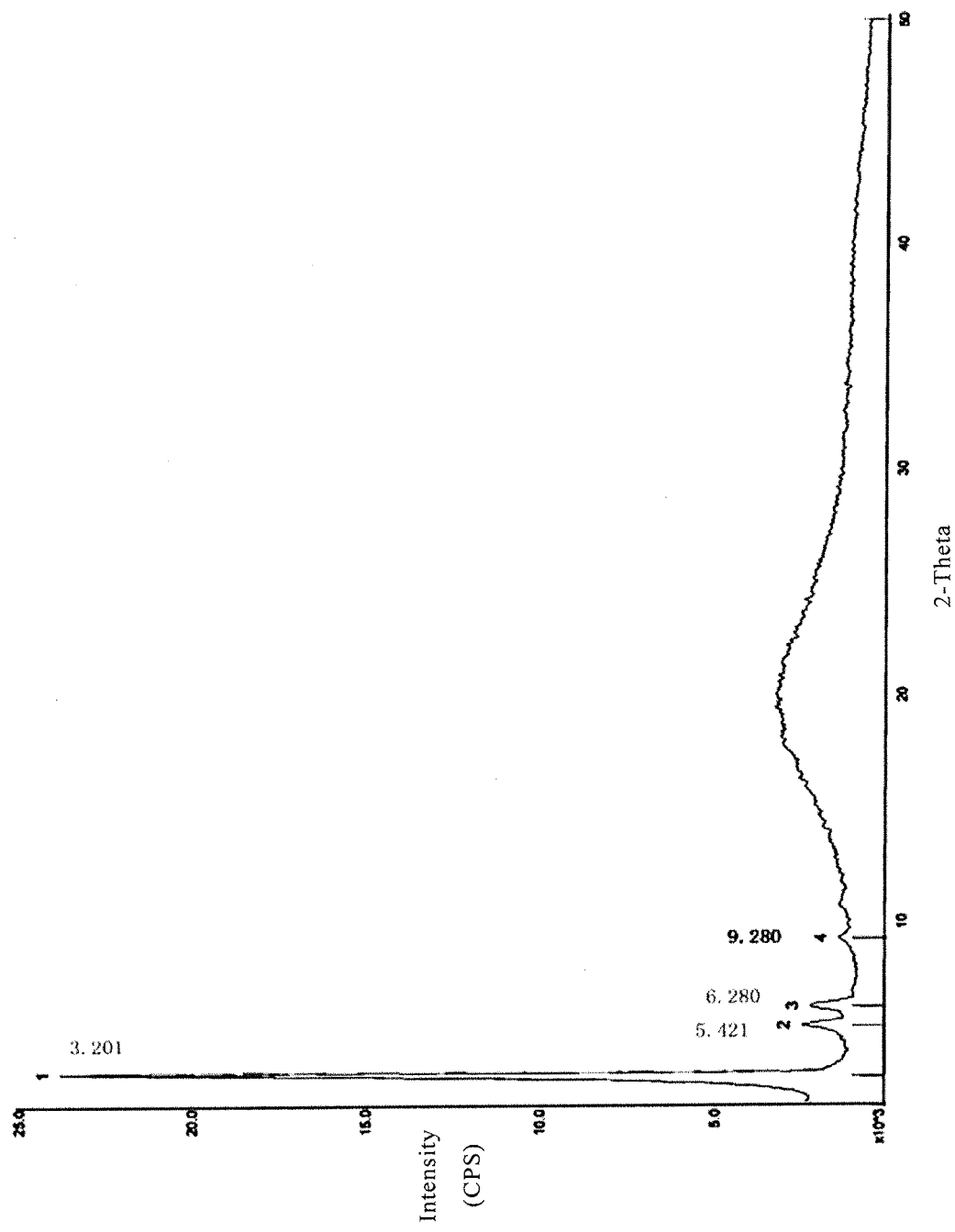

FIG. 4 shows the X-ray powder diffraction pattern of crystalline form of compound I obtained in Comparative Example of the invention;

MODES FOR CARRYING OUT THE INVENTION

Upon research, the inventors have discovered that a single crystalline form A of compound I can be obtained by: dissolving compound I into methanol, acetonitrile, ethyl acetate, methyl acetate, isopropyl acetate, and t-butyl acetate or the combinations thereof to form a homogeneous solution, and then performing crystallization and changing such factors as the temperature of crystallization, mol concentration, cooling rate or stirring speed. Alternatively, a single crystalline form A of compound I can be obtained by: dissolving compound I into methanol, acetonitrile, ethyl acetate, methyl acetate, isopropyl acetate, and t-butyl acetate or the combinations thereof to form a homogeneous solution, diluting the solution of compound I using a poor solvent, such as pentane, n-hexane, cyclohexane, heptane, or the combinations thereof or water, performing crystallization and changing such factors as the temperature of crystallization, mol concentration, cooling rate and stirring speed, or crystallization time. Crystalline form A is a stable crystalline form, and high yield of crystallization can be obtained by such method.

As used herein, the chemical formula or name shall include all optical isomers and stereoisomers as well as racemic mixtures comprising these isomers and mixtures thereof.

Crystalline Form A of Compound I

Upon research, the inventors have surprisingly discovered that a single crystalline form A of compound I can be obtained by mixing compound I with a polar solvent to form a homogeneous solution, and then changing such factors as the temperature of crystallization, mol concentration, stirring speed; alternatively, by mixing compound I with a polar solvent to form a homogeneous solution, diluting the resulting solution using a poor solvent, and then changing such factors as the temperature of crystallization, mol concentration, stirring speed, which demonstrates that crystalline form A is a unique advantageous crystalline form. Then, a sample of compound I with low residual solvent, even without residual solvent, can be obtained by simple drying methods. Therefore, the defect of excess of residual solvent, and the difficulties in sampling as well as split charging can be overcome. Moreover, the inventors have surprisingly discovered that crystalline form A of compound I has a unique stability which is favorable to preservation.

In the present invention, crystalline form A of the compound of formula I is provided, and the properties thereof were studied using a variety of methods and instruments.

I

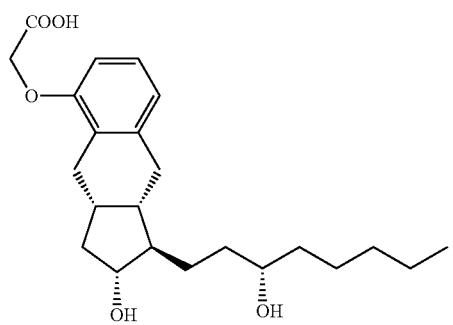

I

X-ray powder diffraction, namely X-ray polycrystal diffraction, is a commonly used experimental method for determining the crystalline structure (i.e., crystalline form). A series of X-ray diffraction patterns can be produced by using X-ray powder diffractometer, when X-ray passing through a crystal. In the pattern, different diffraction lines and the intensities thereof are determined by atomic cluster having certain structure. Therefore the specific structure of a crystalline form can be determined.

The methods for determining the X-ray diffraction pattern of a crystalline form are known in the art. For example, the pattern can be obtained by using Bruker D8 Advanced X-ray powder diffractometer with the scanning rate of 2°/min and copper irradiated target being used.

Figure 1:
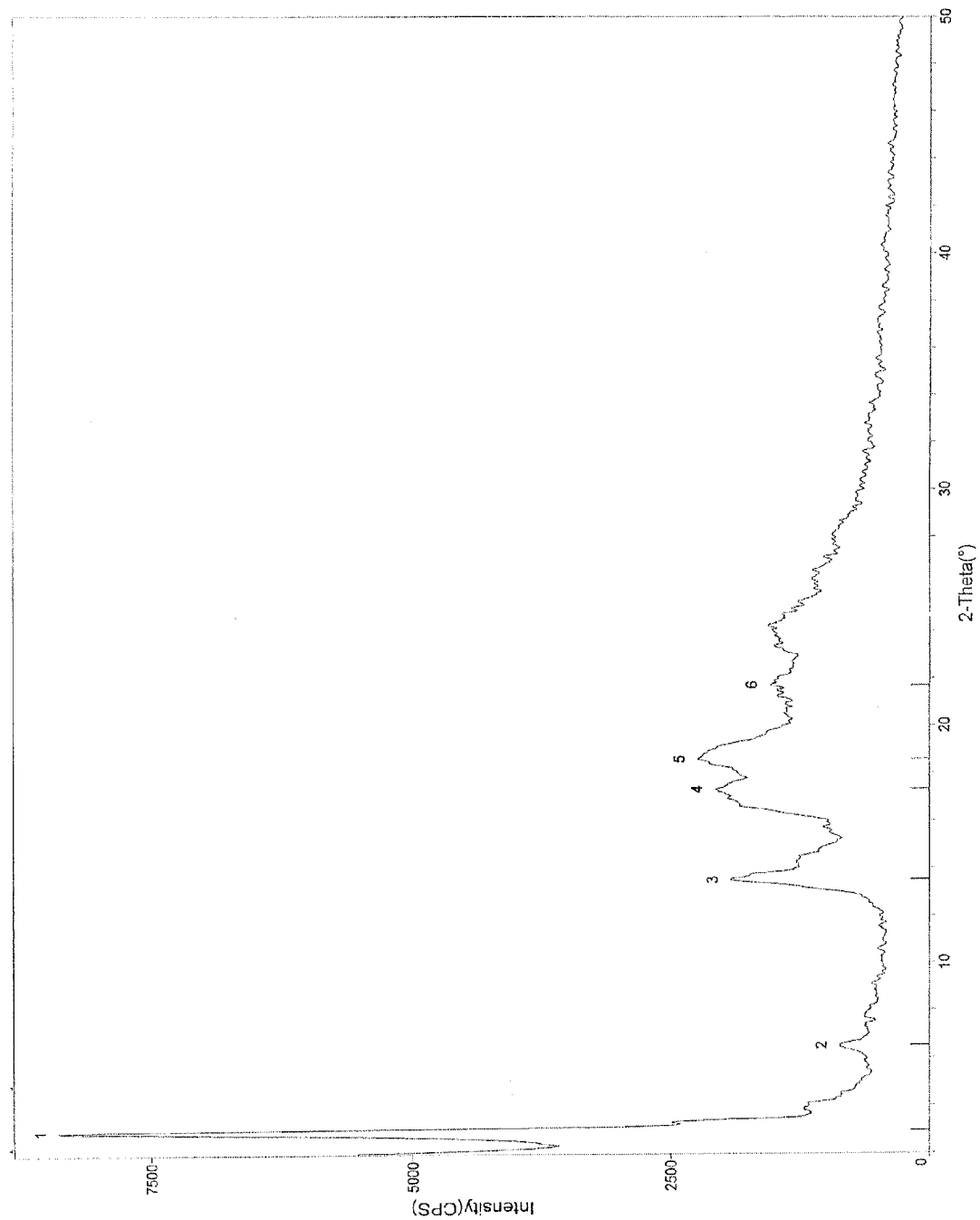
FIG. 1 shows the X-ray powder diffraction pattern of crystalline form A of compound I obtained in Examples of the invention.

The crystalline form A of compound I according to the present invention possesses the unique crystal form and specific characteristic peaks in the X-ray powder diffraction (XRPD) pattern. Particularly, the crystalline form A of compound I according to the present invention possesses characteristic peaks at the following 2θ angles in the X-ray powder diffraction (XRPD) pattern:2.9±0.2°, 13.6±0.2°, 17.3±0.2° and 18.6±0.2°; and preferably, further possesses characteristic peak at the following 2θ angle: 21.8±0.2°. Most preferably, said crystalline form A possesses the X-ray powder diffraction (XRPD) pattern substantially identical with FIG. 1.

"Differential scanning calorimetry" (DSC) is a technology for measuring the relationship of energy difference and temperature between the tested substance and the reference during the heating process. On the DSC pattern, the location, form and number of the peak are relevant to the properties of the substance; therefore, the substance can be qualitatively identified by using DSC. Said method is used in the art to detect many parameters of a substance, such as the phase transition temperature, glass transition temperature and reaction heat.

DSC is known in the art. For example, DSC pattern of a crystal can be obtained by using DSC Q20 differential scanning calorimeter under the following conditions: warming rate of 10° C./min, from 25° C. to 200° C.

In one embodiment of the present invention, the crystalline form A of compound I obtained by the method according to the present invention was determined to have the maximum peak at 120-130° C. by DSC; preferably, at 124.84° C.; and more preferably, the crystalline form A of compound I according to the present invention has the DSC pattern substantially identical with FIG. 2.

The crystal structure can also be determined by Infrared Spectrometry (IR), which is known in the art. For example, it can be determined by using PE Spectrum One B, tableting at KBr: sample=200:1, and scanning 400~4000 cm$^{-1}$. The crystalline form A of compound I according to the present invention has characteristic peaks at the following wave numbers: 3432.44 cm$^{-1}$, 3380.48 cm$^{-1}$, 3307.00 cm$^{-1}$, 2929.82 cm$^{-1}$, 2854.72cm$^{-1}$, 2590.52 cm$^{-1}$, 1936.53 cm$^{-1}$, 1740.01 cm$^{-1}$, 1711.90 cm$^{-1}$, 1607.45 cm$^{-1}$, 1584.91 cm$^{-1}$, 1469.58 cm$^{-1}$, 1423.93 cm$^{-1}$, 1327.64cm$^{-1}$, 1310.81 cm$^{-1}$, 1258,89 cm$^{-1}$, 1147.72 cm$^{-1}$, 1122.09 cm$^{-1}$, 1082.36 cm$^{-1}$, 1026.45 cm$^{-1}$, 890.36 cm$^{-1}$, 788.35 cm$^{-1}$, 776.19 cm$^{-1}$, 737.98 cm$^{-1}$. Preferably, the crystal has the IR pattern substantially identical with FIG. 3.

Preparation Method for Crystalline Form A of Compound I

The present invention also provides a method for preparing crystalline form A of the compound of formula I.

In one embodiment provided in the present invention, a preparation method for the crystalline form A of compound I comprises the following steps:

(1) the crude compound of formula I is mixed with solvent 1 to obtain solution 1; and solvent 1 is selected from the following: methanol, acetonitrile, ethyl acetate, methyl acetate, isopropyl acetate, and/or t-butyl acetate;

(2) solution 1 is cooled or solvent 2 is added and stirred to give the crystalline form A of compound I.

In step (1), the mixing should be carried out below the boiling point of solvent 1, preferably at 0-80° C.; more preferably, at 20-50° C.; more preferably, at 30-50° C.

In step (1), the ratio (weight to volume) for mixing the crude compound of formula I and solvent 1 is 1:0.5-50 (g:ml); preferably, 1:0.5-20; more preferably, 1:1-5 (g:ml).

In step (1), solution 1 is a homogeneous solution obtained by thoroughly mixing the crude compound of formula I with solvent 1 and dissolving the compound into solvent 1.

In step (2), the temperature should not be lowered to below the melting point of solution 1, which can be lower than the temperature for mixing in step (1) by 25-80° C.; and preferably, can be lowered to −25° C. to 25° C.; more preferably, to −5° C. to 5° C.; and more preferably, to −2° C. to 2° C.

Solvent 2 can be one or more selected from the following group: water, and C5-C8 alkane; preferably, selected from n-hexane, n-heptane, cyclohexane, methyl tert-butyl ether and/or petroleum ether.

The volume ratio of solvent 2 in steps (2) to solvent 1 in step (1) is 0.1-1:1; preferably, 0.2-0.8:1; and more preferably, 0.4-0.6:1.

In step (2), after solvent 2 is added, the resulting mixture is cooled to 1 to 10° C., and then is stirred for 5-50 hours; and preferably, cooled to 3 to 7° C., and then is stirred for 10-30 hours.

More preferably, in said embodiment, step (3) can be included posterior to step (2), the crystalline form A of compound 1 is filtered, the filter cake is washed by using solvent 1 and dried under reduced pressure to give a solid of crystalline form A of compound I.

In step (3), washing can be performed according to routine methods in the art, the purpose for which is to remove a few impurities, i.e., remove impurities adhering to the surface of crystals by washing.

Use of Crystalline Form A of Compound I

Crystalline form A of compound A of compound I provided by the present invention has good stability, and can be used as raw material medicament for the treatment of pulmonary hypertension and peripheral vascular disease.

The medicament comprises crystalline form A of the compound of formula I and a pharmaceutically acceptable carrier. Depending on the route of administration, the medicament can be prepared into various dosage forms. The dosage forms can be administered through one of the following routes: oral, inhalation, transdermal, etc. Moreover, it is necessary to be noted that the dosage and methods of use of crystalline form A of compound I according to the present invention depend on various factors, including the age, weight, gender, natural health status, nutritional status of the patient, intensity of activity of compound, administration, metabolic rate, the severity of the disease and attending physician's subjective judgment.

As used herein, "crude compound of formula I" means compound of formula I in amorphous form prepared by the methods known in the art. Preferably, the crude compound I without purification can be prepared by the method reported in J. Org. Chern. 2004, 69, 1890-1902, and using (1R, 2R, 3aS, 9aS)-2,3,3a,4,9,9a-hexahydro-1-[(3S)-3-hydroxyoctyl]-1H-phenyl[f]indene-2,5-diol as a starting material.

As used herein, "HPLC purity" refers to the percentage of the peak area of compound I obtained by area normalization method in the sum of all the peak area in HPLC detection applied to compound I, according to the obtained chromatogram.

Column: 4.6×250 mm 5 μm C18 column; flow rate: 2 ml/min; injection volume: 10 μl; column temperature: 35° C.; detection wavelength: 217 nm; mobile phase: acetonitrile/water/trifluoroacetic acid; detection limit: 10 ng.

As used herein, the term "pharmaceutically acceptable carrier" refers to a carrier for the administration of therapeutic agents, including various excipients and diluents. This term refers to such pharmaceutical carriers that they are not necessary active ingredients, and won't cause undue toxicity upon administration. Suitable carriers are well-known to the skilled person in the art. Detailed discussion on the pharmaceutically acceptable excipients can be found in Remington's Pharmaceutical Sciences (Mack Pub. Co., NJ 1991). In a composition, a pharmaceutically acceptable carrier may include a liquid, such as water, saline, glycerol and ethanol. Moreover, there may be auxiliary substances, such as disintegrants, wetting agents, emulsifying agents, pH buffering substances and the like in these carriers.

All the features mentioned above or in the examples below of the invention can be optionally combined. All features disclosed in this specification may be used in any combination. Any alternative feature serving the same, equivalent, or similar purpose may replace each feature disclosed in this specification. Therefore, unless otherwise specified, the features as disclosed are only general examples of equivalent or similar features.

The main advantages of the invention include:

1. Crystalline form A of the present invention has a unique stability,
2. The defect of cryopreservation for compound I can be overcome based on the specific crystalline form provided by the present invention.

The invention will be further illustrated with reference to the following specific examples. It is to be understood that these examples are only intended to illustrate the invention, but not to limit the scope of the invention. For the experimental methods in the following examples without particular conditions, they are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

HPLC detection method mentioned in the following Examples are listed as follows:

Column: 4.6×250 mm 5 μm C18 column; flow rate: 2 ml/min; injection volume: 10 μl; column temperature: 35° C.; detection wavelength: 217 nm; mobile phase: acetonitrile/water/trifluoroacetic acid; Elution condition: water (60%): acetonitrile (40%): trifluoroacetic acid (0.1%); detection limit: 10 ng.

The purity mentioned in the following Examples is HPLC purity.

Example 1

Preparation of the Crude Compound I

The crude compound I (41 g) without purification can be prepared by the method reported in J. Org. Chern. 2004, 69, 1890-1902, and using (1R,2R,3aS,9aS)-2,3,3a,4,9,9a-hexahydro-1-[(3S)-3-hydroxyoctyl]-1H-phenyl[f]indene-2,5-diol as a starting material.

Comparable Example 2

1.0 g of the crude compound was crystallized in ethanol/water (1:1) according to the method reported in J. Org. Chern. 2004, 69, 1890-1902, to give a gummy solid (0.71 g). The purity of solid is 99.23%, and the X-ray powder diffraction pattern thereof is shown in FIG. 4.

Comparable Example 3

1.0 g of the crude compound was crystallized and dried according to the method reported in WO2009137066 to give a gummy solid (0.73 g). The purity of solid is 99.39%.

Example 4

Preparation of Crystalline Form A of Compound I

Into a 25 ml eggplant shaped bottle, was added the crude compound I obtained in Example 1 (1.0 g) and methanol (1.0 ml). The temperature was increased to 30° C. for dissolving the crude compound to give a homogeneous solution. Pure water (0.6 ml) was slowly added. The solution was cooled to 5° C. and stirred for 10 h. The precipitate was filtered off, washed by 10% aqueous solution of methanol for 2-3 times at 5° C., and dried to give 0.91 g of crystalline solid. For the solid, X-ray powder diffraction pattern is consistent with FIG. 1, Differential Scanning calorimetry (DSC) is consistent with FIG. 2, and Infrared Spectrometry is consistent with FIG. 3, and HPLC purity is 99.90%. Organic residue: methanol 0.04% (yield: 91%).

Example 5

Preparation of Crystalline Form A of Compound I

Into a 25 ml eggplant shaped bottle, was added the crude compound I obtained in Example 1 (1.0 g) and ethyl acetate (5.0 ml). The temperature was increased to 40° C. for dissolving the crude compound to give a homogeneous solution. And the solution was cooled to 0° C. and stirred for 12 h. The precipitate was filtered off, washed by ethyl acetate for 2-3 times at 0° C., and dried to give 0.85 g of crystalline solid. For the solid, X-ray powder diffraction pattern is consistent with FIG. 1, Differential Scanning calorimetry (DSC) is consistent with FIG. 2, and Infrared Spectrometry is consistent with FIG. 3, and HPLC purity is 99.74%. Organic residue: ethyl acetate 0.03% (yield: 85%).

Example 6

Preparation of Crystalline Form A of Compound I

Into a 25 ml eggplant shaped bottle, was added the crude compound I obtained in Example 1 (1.0 g) and ethyl acetate (4.0 ml). The temperature was increased to 40° C. for dissolving the crude compound. N-hexane (2 ml) was added at the same temperature dropwise. And the resulting mixture was cooled to 3° C. and stirred for 20 h. The precipitate was filtered off, washed by ethyl acetate and n-hexane (1:1) for 2-3 times at 5° C., and dried to give 0.98 g of crystalline solid. For the solid, X-ray powder diffraction pattern is consistent with FIG. 1, Differential Scanning calorimetry (DSC) is consistent with FIG. 2, and Infrared Spectrometry is consistent with FIG. 3, and HPLC purity is 99.50%. Organic residue: ethyl acetate 0.04%, n-hexane 0.01% (yield: 98%).

Example 7

Preparation of Crystalline Form A of Compound I

Into a 25 ml eggplant shaped bottle, was added the crude compound I obtained in Example 1 (1.0 g) and ethyl acetate (3.0 ml). The temperature was increased to 50° C. for dissolving the crude compound to give a homogeneous solution. N-heptane (1.2 ml) was added at the same temperature dropwise. And the resulting mixture was slowly cooled to 7° C. and stirred for 30 h. The precipitate was filtered off, washed by ethyl acetate and n-hexane (2:1) for 2-3 times at 5° C., and dried to give 0.68 g of crystalline solid. For the solid, X-ray powder diffraction pattern is consistent with FIG. 1, Differential Scanning calorimetry (DSC) is consistent with FIG. 2, and Infrared Spectrometry is consistent with FIG. 3, and HPLC purity is 99.80%. (yield: 68%).

Example 8

Preparation of Crystalline Form A of Compound I

Into a 25 ml eggplant shaped bottle, was added the crude compound I obtained in Example 1 (1.0 g) and methyl acetate (3.5 ml). The temperature was increased to 40° C. for dissolving the crude compound to give a homogeneous solution. And the solution was slowly cooled to −2° C. and stirred for 25 h. The precipitate was filtered off, washed by methyl acetate for 2-3 times at 0° C., and dried to give 0.84 g of crystalline solid. For the solid, X-ray powder diffraction pattern is consistent with FIG. 1, Differential Scanning calorimetry (DSC) is consistent with FIG. 2, and Infrared Spectrometry is consistent with FIG. 3, and HPLC purity is 99.80% (yield: 84%).

Example 9

Preparation of Crystalline Form A of Compound I

Into a 25 ml eggplant shaped bottle, was added the crude compound I obtained in Example 1 (1.0 g) and isopropyl acetate (3.0 ml). The temperature was increased to 50° C. for dissolving the crude compound to give a homogeneous solution. Cyclohexane (0.6 ml) was added at the same temperature dropwise. And the resulting mixture was slowly cooled to 5° C. and stirred for 30 h. The precipitate was filtered off, washed by isopropyl acetate and cyclohexane (2:1) for 2-3 times at 5° C., and dried to give 0.72 g of crystalline solid. For the solid, X-ray powder diffraction pattern is consistent with FIG. 1, Differential Scanning calorimetry (DSC) is consistent with FIG. 2, and Infrared Spectrometry is consistent with FIG. 3, and HPLC purity is 99.50% (yield: 72%).

Example 10

Preparation of Crystalline Form A of Compound I

Into a 25 ml eggplant shaped bottle, was added the crude compound I obtained in Example 1 (1.0 g) and ethyl acetate (4.0 ml). The temperature was increased to 40° C. for dissolving the crude compound to give a homogeneous solution. Methyl tert-butyl ether (0.8 ml) was added at the same temperature dropwise. And the resulting mixture was slowly cooled to −5° C. and stirred for 20 h. The precipitate was filtered off, washed by ethyl acetate and methyl tert-butyl ether (2:1) for 2-3 times at 5° C., and dried to give 0.86 g of crystalline solid. For the solid, X-ray powder diffraction pattern is consistent with FIG. 1, Differential Scanning calorimetry (DSC) is consistent with FIG. 2, and Infrared Spectrometry is consistent with FIG. 3, and HPLC purity is 99.55% (yield: 86%).

Example 11

Preparation of Crystalline Form A of Compound I

Into a 25 ml eggplant shaped bottle, was added the crude compound I obtained in Example 1 (1.0 g) and t-butyl acetate (3.0 ml). The temperature was increased to 50° C. for dissolving the crude compound to give a homogeneous solution. Petroleum ether (1.2 ml) was added at the same temperature dropwise. And the resulting mixture was slowly cooled to 5° C. and stirred for 30 h. The precipitate was filtered off, washed by t-butyl acetate and petroleum ether (2:1) for 2-3 times at 5° C., and dried to give 0.80 g of crystalline solid. For the solid, X-ray powder diffraction pattern is consistent with FIG. 1, Differential Scanning calorimetry (DSC) is consistent with FIG. 2, and Infrared Spectrometry is consistent with FIG. 3, and HPLC purity is 99.62% (yield: 80%).

Example 12

Preparation of Crystalline Form A of Compound I

Into a 25 ml eggplant shaped bottle, was added the crude compound I obtained in Example 1 (0.1 g) and acetonitrile (4.5 ml). The temperature was increased to 50° C. for dissolving the crude compound to give a homogeneous solution. And the solution was slowly cooled to 2° C. and stirred for 10 h. The precipitate was filtered off, washed by acetonitrile for 2 times at 0° C., and dried to give 0.85 g of crystalline solid. For the solid, X-ray powder diffraction pattern is consistent with FIG. 1, Differential Scanning calorimetry (DSC) is consistent with FIG. 2, and Infrared Spectrometry is consistent with FIG. 3, and HPLC purity is 99.60% (yield: 85%).

Example 13

Stability Comparison

Compound I from example 2, example 3 and example 4 were obtained, and subjected to stability test at 40° C., respectively. The HPLC results demonstrated that crystalline form A of compound I did not degrade at all, after stored at 0° C. for 12 months, at 20° C. for 6 months, or at 40° C. for 2 months.

Therefore, crystalline form A of compound I prepared by the method of the present invention has unique stability.

| Crystalline Form | Purity at 0 day (40° C.) | Purity at 10 day (40° C.) | Purity at 30 day (40° C.) | Purity at 90 day (40° C.) |
|---|---|---|---|---|
| Exampl 2 | 99.23% | 99.23% | 99.15% | 98.63% |
| Example 3 | 99.39% | 99.38% | 99.31% | 99.09% |
| Example 4 | 99.90% | 99.91% | 99.89% | 99.88% |

Example 14

Pharmaceutical Composition

Crystalline form A of compound I prepared in Example 2 (17.4 mg), sodium chloride (189 mg), sodium citrate (183 mg), sodium hydroxide (5.8 mg), and 1 N HCl (117 mg) were mixed into 20 ml of pure water. And then pure water was supplemented to the final volume of 29 ml. The mixture was divided into 10 aliquots, and the aliquots were added into 3 ml ampoule bottles (n=10), respectively. Each ampoule was loaded into a nebulizer for treating pulmonary hypertension or peripheral vascular disease by inhalation.

The above examples are merely the preferred examples for the present invention, and such examples cannot be used to limit the scope of the invention. The substantial technical contents according to the present invention are broadly defined in the claims. And any entities or methods accomplished by others should be considered as the equivalents and fall within the scope as defined by the claims, if said entities or methods are the same as those defined by the claims.

What we claimed is:

1. Crystalline form A of a compound, wherein the compound has the structure of formula I, and said crystalline form A has characteristic peaks at the following 2θ angles in the X-ray Powder diffraction (XRPD) pattern: 2.9±0.2°, 13.6±0.2°, 17.3±0.2° and 18.6±0.2°;

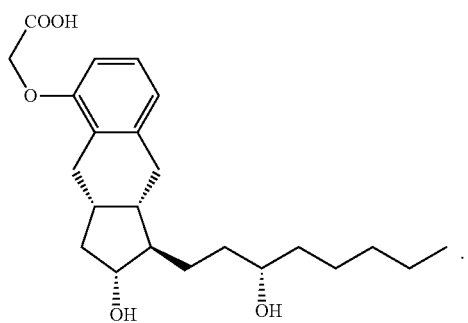

2. The crystalline form A of the compound according to claim 1, wherein said crystalline form A may has other characteristic peak at the following 2θ angle in the X-ray powder diffraction pattern: 21.8±0.2°.

3. The crystalline form A of the compound according to claim 1, wherein the maximum peak in the differential scanning calorimetry (DSC) for said crystalline form A exists at 123° C. -128° C.; and preferably, at 125° C.

4. The crystalline form A of the compound according to claim 3, wherein the differential scanning calorimetry (DSC) for said crystalline form A is shown as in FIG. 2.

5. The crystalline form A of the compound according to claim 1, wherein Infrared Spectrum of said crystalline form A is shown in FIG. 3.

6. A preparation method for crystalline form A of compound I according to claim 1, comprising the following steps:
(1) the crude compound of formula I is mixed with one or more solvents selected from following solvent 1 to obtain solution 1: methanol, acetonitrile, ethyl acetate, methyl acetate, isopropyl acetate, and t-butyl acetate;
(2) solution 1 is stirred and cooled, or solvent 2 is added to give the crystalline form A of compound I according to claim 1, wherein said solvent 2 is selected from one or more of the following: water, and C5-C8 alkane.

7. The preparation method according to claim 6, wherein, in step (1), the temperature for mixing is at 0-80° C.; preferably, at 20-50° C.; more preferably, at 30-50° C.

8. The preparation method according to claim 6, wherein, in step (1), the weight to volume ratio for mixing the crude compound of formula I and the solvent 1 is 1:0.5-50 (g:ml); preferably, 1:0.5-20 (g:ml); more preferably, 1:1-5 (g: ml).

9. The preparation method according to claim 6, wherein, in step (2), the temperature is cooled to −25° C. to 25° C.; preferably, −5° C. to 5° C.; more preferably, −2° C. to 2° C.

10. The preparation method according to claim 6, wherein, in step (2), after cooled, the solution is stirred for 5-50 hours; preferably, 10-30 hours; and more preferably, 12-25 hours.

11. The preparation method according to claim 6, wherein, the volume ratio of solvent 2 in steps (2) to solvent 1 in step (1) is 0.1-1:1; preferably, 0.2-0.8:1; more preferably, 0.4-0.6:1.

12. The preparation method according to claim 6, wherein, in step (2), after solvent 2 is added, the resulting mixture is cooled to 1 to 10° C., and then is stirred for 5-50 hours; and preferably, cooled to 3 to 7° C., and then is stirred for 10-30 hours.

13. A pharmaceutical composition, wherein said pharmaceutical composition comprises crystalline form A of compound I according to claim 1 and a pharmaceutically acceptable carrier.

* * * * *